(12) United States Patent
Ransom

(10) Patent No.: US 8,688,219 B2
(45) Date of Patent: Apr. 1, 2014

(54) DYNAMIC SAMPLING

(75) Inventor: Scott A. Ransom, Marysville, WA (US)

(73) Assignee: Medronic, Inc., Minneapolis, MN (US)

( * ) Notice: Subject to any disclaimer, the term of this patent is extended or adjusted under 35 U.S.C. 154(b) by 2366 days.

(21) Appl. No.: 11/460,670

(22) Filed: Jul. 28, 2006

(65) Prior Publication Data
US 2008/0027502 A1 Jan. 31, 2008

(51) Int. Cl.
A61N 1/18 (2006.01)

(52) U.S. Cl.
USPC .................................. 607/42; 600/529; 607/2

(58) Field of Classification Search
USPC ............... 600/529, 554; 607/2, 16, 42, 48, 62
See application file for complete search history.

(56) References Cited

U.S. PATENT DOCUMENTS

| | | | |
|---|---|---|---|
| 4,407,296 A | 10/1983 | Anderson | |
| 4,485,813 A | 12/1984 | Anderson et al. | |
| 5,123,425 A | 6/1992 | Shannon et al. | |
| 5,127,402 A | 7/1992 | Mann et al. | |
| 5,174,287 A | 12/1992 | Kallok | |
| 5,178,156 A | 1/1993 | Takishima et al. | |
| 5,190,053 A | 3/1993 | Meer | |
| 5,211,173 A | 5/1993 | Kallok et al. | |
| 5,215,082 A | 6/1993 | Kallok et al. | |
| 5,271,395 A | 12/1993 | Wahlstrand et al. | |
| 5,320,643 A | 6/1994 | Roline et al. | |
| 5,441,524 A | 8/1995 | Rueter et al. | |
| 5,464,432 A | 11/1995 | Infinger et al. | |
| 5,540,731 A | 7/1996 | Testerman | |
| 6,167,303 A | 12/2000 | Thompson | |
| 6,185,454 B1 | 2/2001 | Thompson | |
| 6,236,888 B1 * | 5/2001 | Thompson | 607/16 |
| 6,336,812 B1 * | 1/2002 | Cooper et al. | 434/267 |
| 6,766,193 B1 | 7/2004 | Mouchawar et al. | |
| 7,292,168 B2 * | 11/2007 | Wesselink et al. | 341/123 |
| 2003/0204140 A1 * | 10/2003 | Ferek-Patric et al. | 600/439 |
| 2004/0102816 A1 | 5/2004 | Mazar et al. | |
| 2005/0182447 A1 * | 8/2005 | Schecter | 607/2 |
| 2006/0247548 A1 | 11/2006 | Sarkar | |

OTHER PUBLICATIONS

Glenn, Diaphragm Pacing: Present Status, Pace, V.I, pp. 357-370, Jul.-Sep. 1978.
Guileminault, C et al, Idiopathic Hypersomnia Revisited: The Unknown Upper Airway Resistance Syndrome, Sleep Res 20: 251, 1991.
Broniatowski, M et al, Laryngeal Pacemaker II: Electronic Pacing of Reinnervated Posterior Cricoarytenoid Muscles in the Canine, Laryngoscope 95: 1194-98, 1985.

* cited by examiner

Primary Examiner — Carl H Layno
Assistant Examiner — Jennifer Ghand
(74) Attorney, Agent, or Firm — Reed A. Duthler; Stephen W. Bauer

(57) ABSTRACT

Dynamic sampling of physiological parameters based on the next anticipated occurrence of a relatively periodic physiological event. Embodiments of the invention may be used to increase the battery life or effective data storage capacity of implantable medical devices while retaining or improving measurement resolution.

12 Claims, 7 Drawing Sheets

DYNAMIC SAMPLING

BACKGROUND OF THE INVENTION

The present invention relates to implantable medical devices. Some embodiments of the invention more particularly relate to medical devices that employ sensors to measure physiological parameters. Some sensors, such as pressure sensors, acoustic sensors, infrared sensors, impendence sensors and others require power to measure the relevant physiological parameter. Sensing electrodes and other sensors provide a signal that may require power for amplification. In either case, the power consumed by powering or amplifying these sensors may reduce battery life when sensors are employed in implantable medical devices.

Various methods have been employed to modify the sampling rate of sensors in medical devices. Previous methods have triggered an adjustment in sample rate based on the measured value from the sensor. These methods adjust the sample rate based on the onset of an event, usually increasing the sample rate when the measured value crosses some threshold.

DETAILED DESCRIPTION OF EMBODIMENTS OF THE INVENTION

Figure 1:
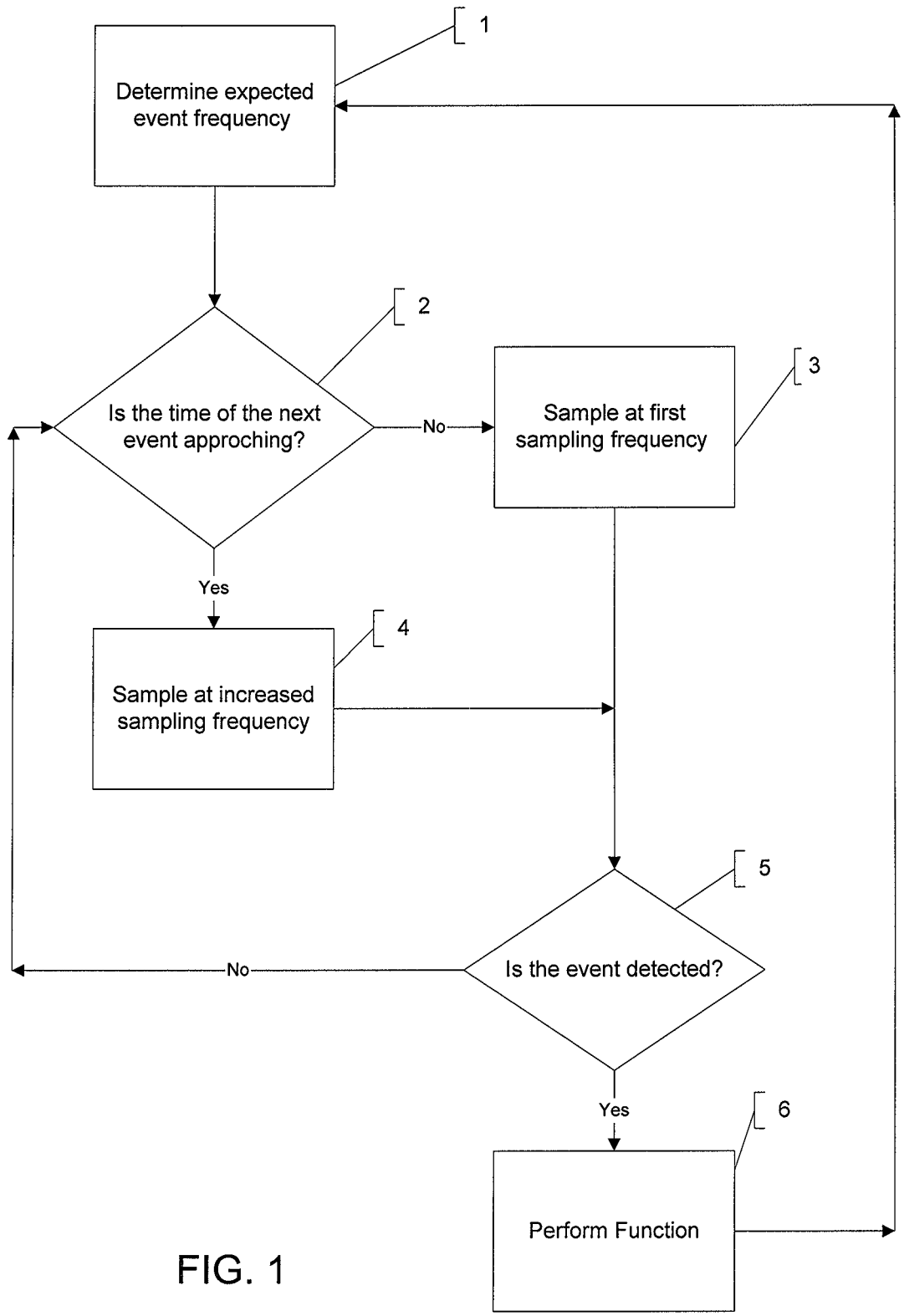
FIG. 1 is a process flow chart of a dynamic sampling routine in accordance with the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Previous methods employed to modify the sampling rate of sensors in medical devices have triggered an adjustment in sample rate based on the measured value from the sensor. While these methods are very useful in some applications, they necessarily have some response lag and do not provide for increases in sample frequency in anticipation of, rather than in response to, an event.

Embodiments of the invention can be useful in treating obstructive upper airway conditions in a patient by detecting inspiratory effort and then stimulating muscles of the upper airway in response to the inspiratory effort. The detection of inspiratory effort may be done with a lower energy demand by using the systems and methods of the invention. This is accomplished by sampling for the detection of inspiratory effort at a lower frequency when inspiration is not anticipated and increasing sampling frequency as the time of the next respiratory cycle approaches.

An implantable pulse generator (IPG) such as a Medtronic ITREL II Model 7424 modified to include an input from a respiratory sensor can be implanted in a patient. The Medtronic ITREL II IPG has advanced programmable features permitting mode changes by transcutaneous RF telemetry. The patient-controllable parameters of the device's operation can therefore be controlled by the patient through a small, hand-held telemetry device while the physician can preset additional operational parameters of the device through an external programmer.

The performance of these embodiments can be improved by selecting a type and location of a respiratory sensor that will allow the device to detect and analyze the respiratory effort of the patient. It has been found that a dynamic dp/dt type of pressure sensor such as that disclosed in U.S. Pat. No. 4,407,296 to Anderson or U.S. Pat. No. 4,485,813 issued to Anderson et al which are hereby incorporated herein by reference in relevant part and can be used for this purpose. This type of pressure sensor is used in the control of heart pacemakers and is known as Medtronic Model 4322. The pressure sensor is surgically implanted at the time of implantation of the IPG in a structure which has pressure coupling with the intrapleural space such as the suprasternal notch, the space between the trachea and esophagus or an intercostal placement. The suprasternal notch is one preferred location for the sensor. The suprasternal notch is a well known structure on the upper chest just above the sternum that is mechanically coupled with the intrapleural space. The pressure sensor can be implanted subcutaneously in the suprasternal notch with leads extending subcutaneously a short distance to the implanted IPG. Another preferred location for the sensor is the space between the trachea and esophagus. It is well known that the rings of cartilage do not completely encircle the trachea. The portion not encircled by cartilage provides a flexible posterior wall to the trachea. The pressure sensor can therefore be surgically implanted at the flexible posterior wall of the trachea, between the trachea and esophagus, without having the sensor invade the airway. In this position, the signal from the pressure sensor can be filtered according to conventional methods to remove short duration artifacts characteristic of activity of the esophagus (e.g. swallowing). Yet another possible location for the pressure sensor is in the venous system such as in the jugular or subclavian veins. Positioning a pressure sensor of this type in the vascular system has been disclosed in connection with the control of heart pacemakers such as in U.S. Pat. No. 5,320,643 to Roline et al. or U.S. Pat. No. 5,271,395 issued to Whalstrand et al. for measurement of such parameters as respiration rate, minute ventilation, and changes in ventricular blood pressure. However, when locating a pressure sensor in the venous system for measurement of respiratory effort, it should be located above the atrium. Conventional filtering of the pressure signal would be required in order to remove blood pressure-related artifacts. Inspiration-synchronous stimulation is then provided from the pulse generator through a lead to an electrode around a nerve.

Embodiments of the invention are not limited to laryngeal pacers, and may also be used whenever relatively predictable repetitive physiological phenomena are monitored such as cardiac electrical events, pressure events within the cardiac cycle, and tissue oxygenation levels.

Many implantable medical devices are powered by batteries that have a limited life. Replacement of these batteries often requires a medical procedure involving some level of expense, patient discomfort, and risk. It is desirable to extend the life of batteries such as these by reducing demands on the batteries without reducing the effectiveness of the device.

Implantable medical devices often employ sensors to measure physiological parameters such as pressure, electrical activity, tissue oxygenation (i.e. using an infrared light source), electrical impedance, physical expansion or movement (i.e. strain gauge), internal body sounds such as blood flow (acoustic sensors). Many of these sensors require relatively significant amounts power each time they measure the physiological parameter of interest. Other sensors may not require significant power for sampling, but may require processing such as analog-to-digital conversion or input amplification that reduce battery life.

Sensors associated with implantable medical devices can be sampled intermittently to reduce power consumption. However, if the sample frequency is too low, important information about the measured physiological parameter may not be detected in a timely manner, or at all. If the sample frequency is too high, the benefits of intermittent sampling are reduced.

Embodiments of the invention include systems that modify the sample frequency of a sensor by using a frequency selector means for increasing the sample frequency in response to the approach of the next expected signal. Systems of the invention provide for sample frequencies that increase based on anticipated physiological activity to ensure a high likelihood of capturing relevant measurements and decrease when relevant physiological activity is not anticipated to reduce power consumption.

Turning now to the Figures, FIG. 1 is a process flow chart of a dynamic sampling routine in accordance with the invention. The first step in the embodiment of FIG. 1 is to determine the expected frequency of a physiological event 1. This may be done by measuring the frequency that a value measured by a sensor crosses a threshold value or by detecting the event of interest directly and measuring the frequency that the event occurs 1. For example, a properly positioned pressure sensor could measure the frequency of a person's respirations by measuring the frequency that a pressure measurement crosses (e.g., exceeds or drops below) a preset threshold. The pressure sensor could also detect the event of interest directly, in this case the onset of inspiration. After observing a number of cycles, the embodiment of FIG. 1 can determine an expected frequency of respiration in the future. This expected frequency is referred to herein as an expected event frequency. This could be determined using a rolling average of the last 5 measured frequencies, for example. Other methods of determining an appropriate expected event frequency will occur to those of skill in the art upon reading this disclosure.

The next step in the embodiment of FIG. 1 is determine if the time of the next event is approaching 2. If, for example, only 20% of the expected signal period has elapsed, the time of the next expected signal is still relatively distant. In most applications, the routine would proceed to step 3 and continue to sample at the first sample frequency. If, on the other hand, something on the order of 80% of the expected signal period had elapsed, the routine may proceed to step 4 and increase the sample frequency in anticipation of the next occurrence of the signal(s) that indicate(s) an event.

As discussed above, this sampling could involve retrieving a value from a sensor or processing or amplifying a value that is provided by a sensor. This first sampling frequency could be considered a baseline sampling frequency and is normally the lowest frequency at which samples are measured or retrieved. All of the sample frequencies discussed herein are application-specific and are set by balancing the desired resolution of the data retrieved against the power demands and/or storage capacity of the devices with which the invention operates.

The step of increasing the sampling frequency 4 may involve an abrupt one-time increase in the sampling frequency. It may also involve, for example, a linear increase in the sample frequency with respect to time, an exponential increase, an asymptotic increase approaching some "maximum" sampling frequency, or any other approach to increasing the sample frequency that may be advantageous for a particular application of the invention.

Whether the sampling frequency is increased or not, the signal from this sample is evaluated to determine if an event has been detected 5. Event detection may consist of comparing the sample to a threshold, evaluating the rate of change of the sample value to a threshold rate of change, or any other known method for determining if a physiological event of interest has occurred. If the signal does indicate the occurrence of an event, the routine again determines if the next expected signal is approaching 2. Until the measured signal detects an event, the routine of FIG. 1 continues to determine if the time of the next expected signal is approaching 3 and adjusts, or does not adjust, the sampling frequency accordingly 3, 4.

Once the signal indicates that an event has occurred, the implantable medical device performs a function 6 that is appropriate in light of the event. The routine then resets and considers the most recent measured frequency in its determination of the expected signal frequency 1.

Embodiments of the invention are useful in the treatment of breathing issues. Because respiration occurs at a relatively predictable frequency, dynamic sampling of a sensor based on the expected occurrence of the next respiratory inspiration event can reduce energy consumption of an implantable medical device such as a laryngeal pacer.

Sleep apnea has been known for some time as a medical syndrome in two generally recognized forms. The first is central sleep apnea, which is associated with the failure of the body to automatically generate the neuro-muscular stimulation necessary to initiate and control a respiratory cycle at the proper time. Work associated with employing electrical stimulation to treat this condition is discussed in Glenn, "Diaphragm Pacing: Present Status", Pace, V. I, pp 357-370 (July-September 1978).

The second sleep apnea syndrome is known as obstructive sleep apnea. Ordinarily, the contraction of the dilator muscles of the upper airways (nose and pharynx) allows their patency at the time of inspiration. In obstructive sleep apnea, the obstruction of the airways results in a disequilibrium between the forces which tend to their collapse (negative inspiratory transpharyngeal pressure gradient) and those which contribute to their opening (muscle contraction). The mechanisms which underlie the triggering of obstructive apnea include a reduction in the size of the superior airways, an increase in their compliance, and a reduction in the activity of the muscle dilator. The muscle dilators are intimately linked to the respiratory muscles and these muscles respond in a similar manner to a stimulation or a depression of the respiratory center. The ventilatory fluctuations observed during sleep (alternately enhancement and depression of periodic respiration) thus favors an instability of the superior airways and the occurrence of oropharyngeal obstruction. The respiratory activation of the genioglossus has been particularly noted to be ineffective during sleep. The cardiovascular consequences of apnea include disorders of cardiac rhythm (bradycardia, auriculoventricular block, ventricular extrasystoles) and hemodynamic (pulmonary and systemic hypertension). This results in a stimulatory metabolic and mechanical effect on the autonomic nervous system. The electroencephalographic awakening which precedes the easing of obstruction of the upper airways is responsible for the fragmentation of sleep. The syndrome is therefore associated with an increased morbidity (the consequence of diurnal hypersomnolence and cardiovascular complications). Other conditions affecting the upper airway are also known such as upper airway resistance syndrome as described in Guilleminault, C, et al, Idiopathic Hypersomnia Revisited: The Unknown Upper Airway Resistance Syndrome, Sleep Res 20: 251, 1991 the relevant parts of which are hereby incorporated herein by reference or vocal cord paralysis as set forth in Broniatowski, M. et al., Laryngeal Pacemaker. II. Electronic Pacing of Reinnervated Posterior Cricoarytenoid Muscles in the Canine, Laryngoscope 95: 1194-98, 1985 which is hereby incorporated herein by reference in relevant part.

A method for treatment of obstructive sleep-apnea syndrome and other upper airway conditions is to generate electrical signals to stimulate those nerves which activate the patient's upper airway muscles in order to maintain upper airway patency. For example, in U.S. Pat. No. 5,540,731 issued to Testerman, inspiratory effort is monitored and electrical signals are directed to upper airway muscles in response to the monitored inspiratory effort. Or, in U.S. Pat. No. 5,123, 425 issued to Shannon et al, a collar contains a sensor to monitor respiratory functioning to detect an apnea episode and an electronics module which generates electrical bursts to electrodes located on the collar. The electrical bursts are transferred transcutaneously from the electrodes to the nerves innervating the upper airway muscles. Or in U.S. Pat. No. 5,174,287 issued to Kallok, sensors monitor the electrical activity associated with contractions of the diaphragm and also the pressure within the thorax and the upper airway. Whenever electrical activity of the diaphragm suggests that an inspiration cycle is in progress and the pressure sensors show an abnormal pressure differential across the airway, the presence of obstructive sleep apnea is assumed and electrical stimulation is applied to the musculature of the upper airway. Or, in U.S. Pat. No. 5,178,156 issued to Takishima et al, respiration sensing includes sensors for sensing breathing through left and right nostrils and through the mouth which identifies an apnea event and thereby triggers electrical stimulation of the genioglossus. Or, in U.S. Pat. No. 5,190,053 issued to Meer, an intra-oral, sublingual electrode is used for the electrical stimulation of the genioglossus to maintain the patency of an upper airway. Or in U.S. Pat. No. 5,211,173 issued to Kallok et al, sensors are used to determine the effectiveness of the stimulation of the upper airway and the amplitude and pulse width of the stimulation are modified in response to the measurements from the sensors. Or in U.S. Pat. No. 5,215,082 issued to Kallok et al, upon sensing of the onset of an apnea event, a stimulation generator provides a signal for stimulating the muscles of the upper airway at a varying intensity such that the intensity is gradually increased during the course of the stimulation. However, even with these modes of therapy there remain many practical difficulties for implementing them in a medically useful treatment system. In particular, if stimulation occurs in response to detected inspiration or to misdetected apnea events, the stimulation may make it difficult for the patient to get to sleep initially or to return to sleep after awakening. According to the Meer U.S. Pat. No. '008 patent, the solution to this problem is to monitor the action potentials of the upper airway muscles to determine when the patent is awake and to commence stimulation only when normal upper airway muscle activity is not detected. However, this approach presents many practical difficulties in implementation and can lead to inappropriate stimulation or failure to stimulate reliably.

Figure 2:
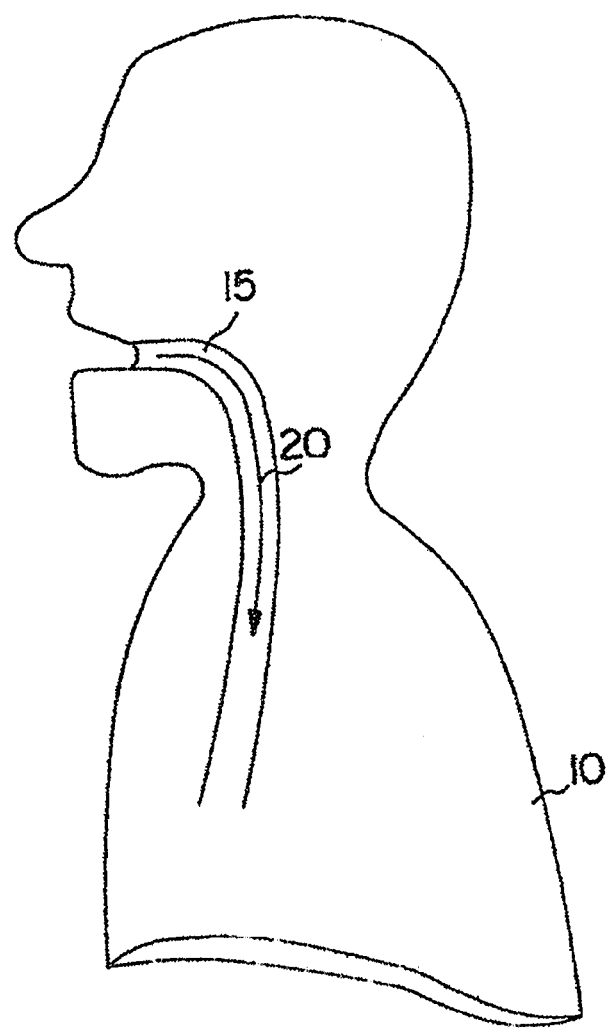
FIG. 2 is a side sectional diagram of a patient having normal respiratory activity.
Figure 3:
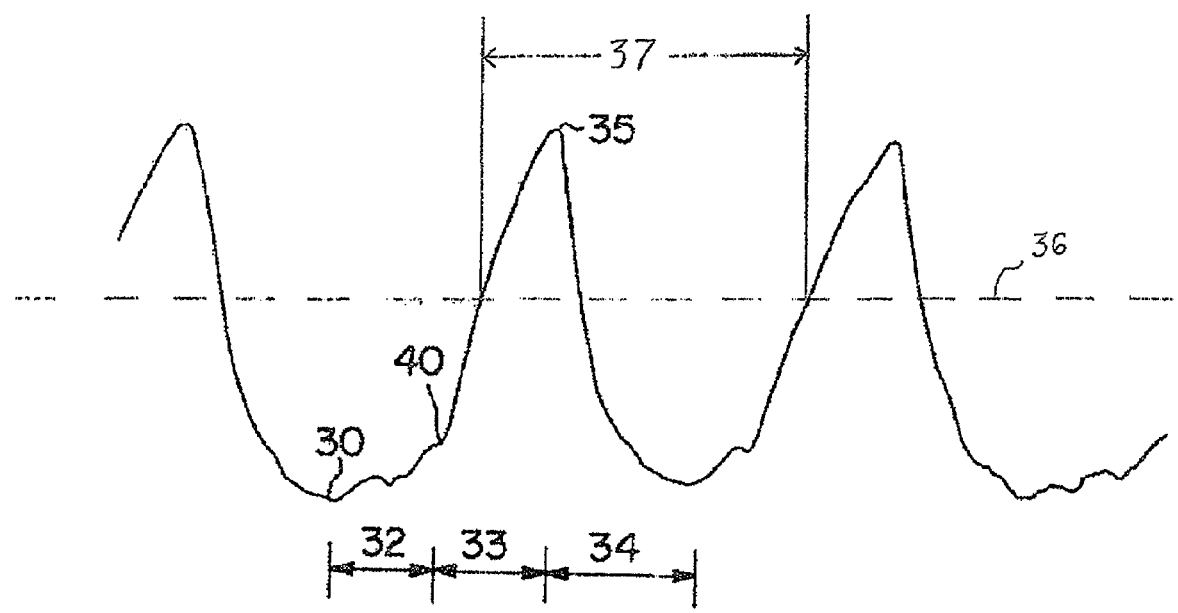
FIG. 3 is a graph of a normal respiratory waveform indicating phases of the respiratory effort waveform.

Embodiments of the present invention are applicable to the treatment of obstructive diseases of the upper airway by administering stimulation of the musculature of the upper airway in synchrony with the inspiratory phase of the respiratory cycle. In FIGS. 2 and 3, normal respiratory activity is depicted. In FIG. 2, a patient 10 has an airway 15 that remains patent during inspiration of air 20. FIG. 3 shows a typical respiratory effort waveform for two complete respiratory cycles. These respiratory cycles comprise a repetitive physiological event that lends itself to a dynamic sampling routine consistent with embodiments of the invention. Each wave of the waveform is characterized by a negative peak 30 on completion of expiration, a positive peak 35 on completion of inspiration and a turning point 40 which indicates the onset of inspiration. Each wave of the waveform can therefore be separated into a period of respiratory pause 32, an inspiratory phase 33, and an expiratory phase 34. When such a wave is monitored by sensors in accordance with the invention, the sampling frequency of the sensor will be lower during the respiratory pause 32 portion of the wave and increase as the onset of the inspiratory phase 33 approaches.

A threshold value 36 may be set by the manufacturer of a laryngeal pacer considering the atmospheric pressure at which the pacer will be used. The threshold value 36 could also be set by a health care provider or patient using prior to implantation of the device or while the device is implanted using telemetry or other communication means. The frequency 37 (inverse of the time period) that the measured value crosses the threshold value 36 (e.g., zero) can be measured by a device. The expected signal frequency of the physiological signal of the onset of respiration can then be calculated by using a moving average of a number of measured frequencies 37. Other characteristics of the waveform could also be identified in connection with tracking and analyzing the respiratory waveform to monitor respiratory activity in upper airway stimulation treatment.

Figure 4:
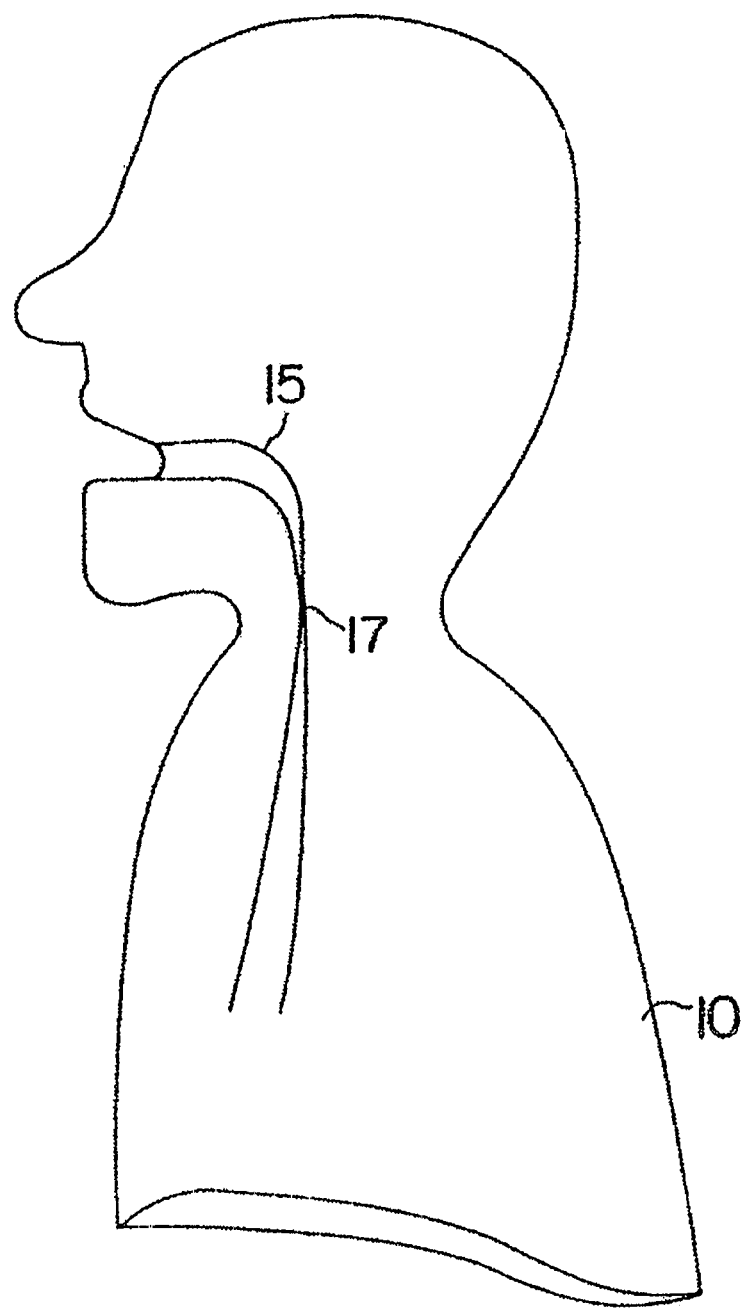
FIG. 4 is a side sectional diagram of the patient of FIG. 2 at the onset of obstructive apnea.
Figure 5:
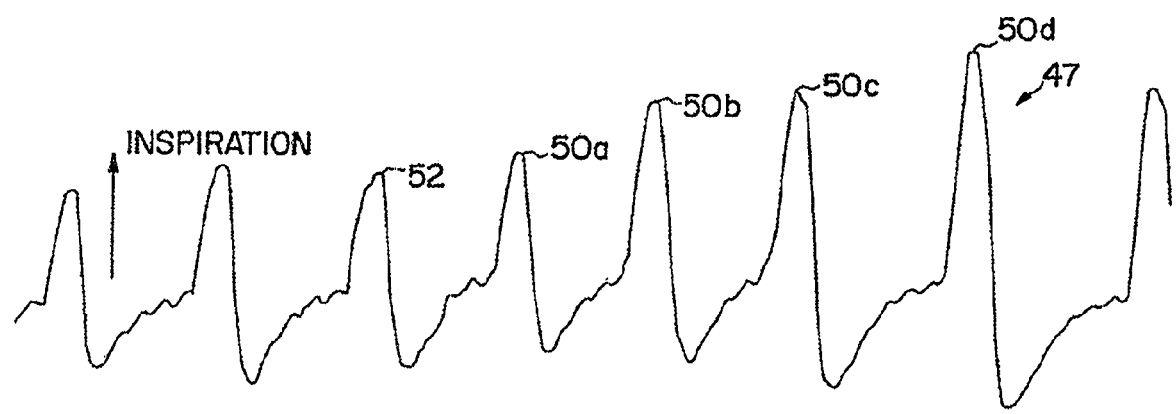
FIG. 5 is a respiratory waveform of inspiratory effort showing the change in normal inspiratory effort at the onset of an apnea event.

In FIGS. 4 and 5, respiration in the same patient at the onset of an obstructive sleep apnea event is depicted. FIG. 4 shows the patient 10 and airway 15 with an airway obstruction 17 that is characteristic of an obstructive apnea event. In FIG. 5 waveform 47 shows inspiratory peaks 50 a-d becoming significantly greater in amplitude at the onset of obstructive apnea than the immediately preceding inspiratory peak 52. This is reflective of the increased inspiratory effort undertaken by the patient in response to the difficulty of breathing through the obstructed airway.

By using a laryngeal pacer, the increased respiratory effort is avoided by synchronized stimulation of one or more muscles in the upper airway which hold the airway open during the inspiratory phase. The muscle or muscles stimulated can be selected from any number of muscles of the upper airway such as the genioglossus muscle which may be stimulated by a cuff electrode placed around the hypoglossal nerve, or by placement of electrodes inferior to the PCA (posterior crico-arytenoid) muscles. A laryngeal pacer employing systems, methods, or computer readable media in accordance with the invention can detect the onset of inspiration while taking fewer energy consuming pressure or other indicating samples.

Figure 6:
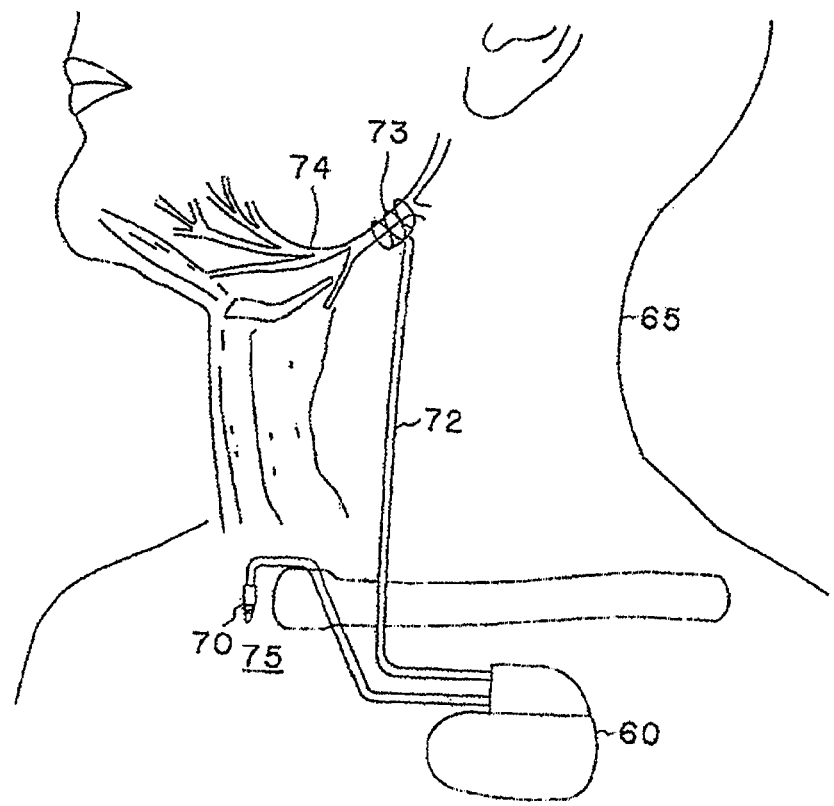
FIG. 6 is an embodiment of the invention using an implanted pulse generator and implanted intrathoracic pressure sensor.

A device operating substantially as described above can be implemented in a fully implantable stimulation system such as that shown in FIG. 6. In FIG. 6, an implantable pulse generator 60 (e.g. a Medtronic ITREL II Model 7424 modified to include an input from a respiratory sensor) can be implanted in a patient 65 with respiratory sensing from a pressure sensor 70. The Medtronic ITREL II implantable IPG has advanced programmable features permitting mode changes by transcutaneous RF telemetry. The patient-controllable parameters of the device's operation can therefore be controlled by the patient through a small, hand-held telemetry device while the physician can preset additional operational parameters of the device such as the threshold pressure 36 described in reference to FIG. 3 through an external programmer. The pressure sensor 70 of this embodiment is a hermetically sealed, implantable device which is dynamic dp/dt type of pressure sensor such as that disclosed in U.S. Pat. No. 4,407,296 to Anderson or U.S. Pat. No. 4,485,813 issued to Anderson et al which are incorporated herein by reference in relevant part. The pressure sensor 70 of this embodiment is surgically implanted in a structure which has pressure coupling with the intrapleural space such as the suprasternal notch, the space between the trachea and esophagus, an intravascular placement or an intercostal placement. Here, it is shown implanted in the suprasternal notch shown generally by numeral 75. The suprasternal notch is a well known structure on the upper chest just above the sternum that is anatomically coupled with the intrapleural space. Inspiration-synchronous stimulation is provided from the pulse generator 60 through a lead 72 to an electrode 73 around the hypoglossal nerve 74.

Figure 7:
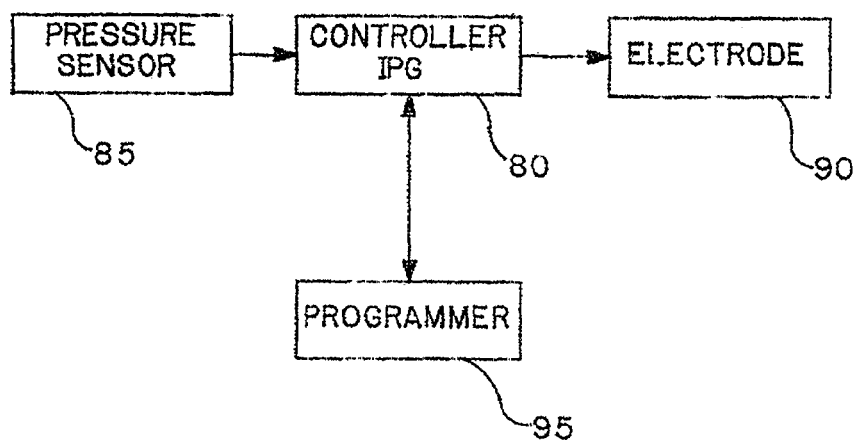
FIG. 7 is a block diagram of one embodiment of the apnea treatment device according to the present invention.

A block diagram of the principal elements of the device is shown in FIG. 7. That device includes a controller 80 which is capable of sensing the inspiratory phase and transmitting an electrical stimulus pulse to muscles of the upper airway. A pressure sensor 85 sends respiratory waveform information to the controller 80 which sends stimulus pulses through an electrode 90 to stimulate the muscles of the patient. The frequency of the sampling of this respiratory waveform information may be modified as described above in reference to FIG. 1. The electrode can be a Medtronic Model 3990 Half Cuff Nerve Electrode or any electrode capable of activating the desired muscle or muscle group. A programmer 95 is capable of remote programming of controller 80 with various parameters in order to adapt the device to a particular patient. The device of FIG. 7 is therefore adapted to be programmed by the doctor and thereafter used each night by the patient to prevent the closure of the upper airway during the inspiratory phase of the respiration cycle. A programmer with basic on/off capabilities may also be provided to the patient in order to allow the patient to enable and disable the preprogrammed treatment. It will be apparent to those skilled in the art that the entire system should be made to be easy to use by the patient and since it is used without constant medical supervision, it must be able to safely adapt to many different operating conditions.

Figure 8:
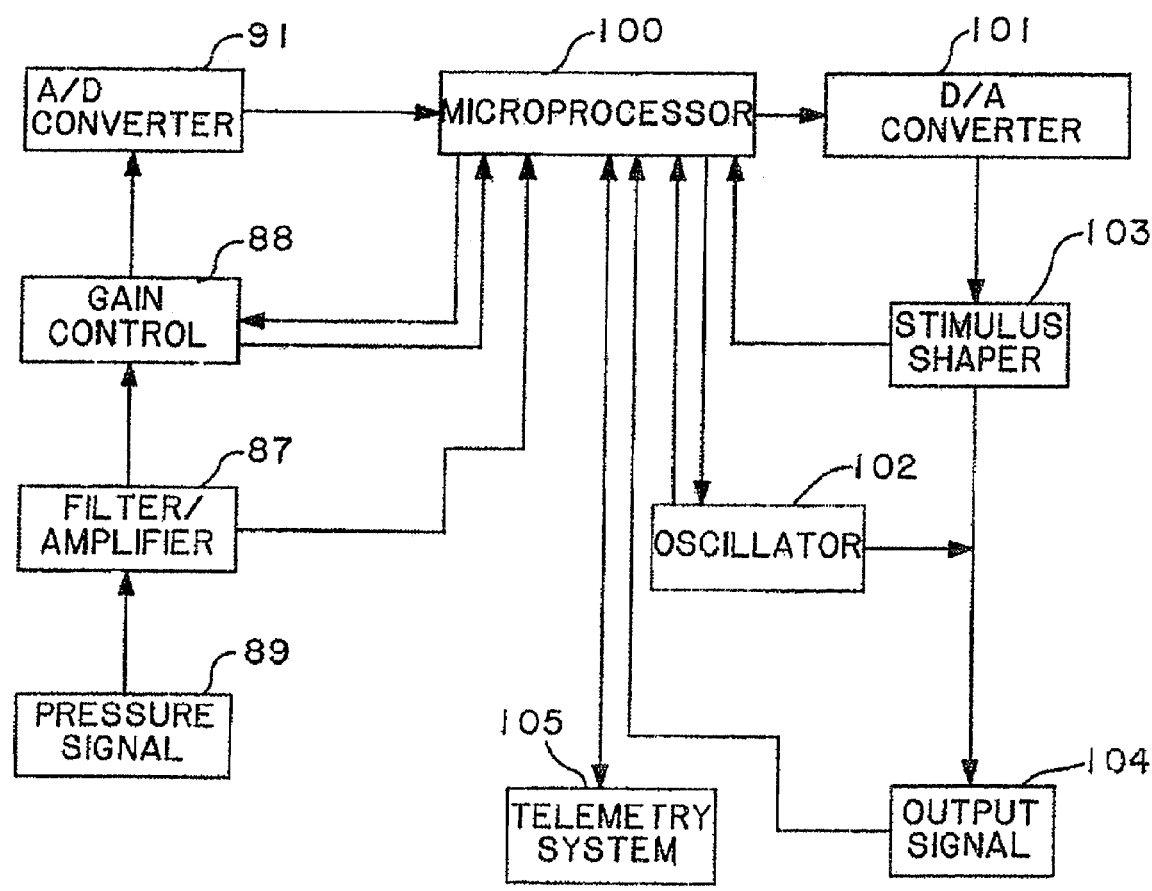
FIG. 8 is a block diagram of the upper airway transmitter/controller of FIG. 7 as it is applied to a patient.

FIG. 8 is a block diagram of the controller 80 of the embodiment of FIG. 7. A microprocessor 100 controls the principal operations of the controller 80. A pressure signal 89 from the pressure sensor 85 is coupled to an amplifier/filter 87 which filters artifacts from the signal 89 and an automatic gain control 88 so that it is compatible with analog or digital signal processing devices such as an analog/digital converter 91. The microprocessor 100 provides data to the D/A converter 101 and the oscillator 102 which allows the stimulus waveform to be shaped by the stimulus shaper 103 into an output signal 104. A telemetry system 105 is used with an external programmer (not shown) to communicate with the microprocessor.

The pressure sensor 85 can be based on a piezoelectric crystal material which acts as a high impedance voltage source in response to deflections of a diaphragm to which it is rigidly attached. Additional electrical components can be included in the sensor, in the IPG and/or in the lead such that the necessary interfacing, signal recovery, and sensor excitation are accomplished. Such a piezoelectric crystal is a device producing a voltage proportional to the rate of mechanical deflection applied to a diaphragm membrane by a physiologic force. It therefore responds to changes in pressure, not to absolute pressure. In operation, a current is provided from the IPG to the lead system which produces an excitation of the sensor. A signal is then recovered from the sensor. The sensor may be sampled at a time interval that is modified based on the time until the next expected onset of inspiration in accordance with embodiments of the invention. The data retrieved from this sampling produces a waveform corresponding to the mechanically applied physiological signal.

When this pressure sensor is implanted in the suprasternal notch, intrathoracic pressure is negative during the inspiratory phase of respiration so that the sensor output is preferably inverted such that inspiration yields a positive-going voltage. At the time a pressure reading is to be taken in one exemplary embodiment, the pulse generator biases the sensor at a current between about 8 .mu.A and 80 .mu.A depending on the output signal required. Since the piezoelectric element of the sensor of this embodiment will only respond to changes in pressure, constant pressure will result in the sensor output returning to a baseline value. Sensitivity of a pressure sensor of this type is about 3 mV/mmHg. The desired operational range for a pressure sensor in accordance with this embodiment is generally between about 1 cmH.sub.2 O and 15 cmH.sub.2 O (i.e. about 3 mV to 60 mV output range) with nominal peak-to-peak values for sensed output of about 5 cmH.sub.2 O (i.e. about 21 mV peak-to-peak centered around a baseline value). The IPG preferably includes an automatic gain/sensitivity control of conventional design to adapt to varying respiration levels and also to patient-to-patient pressure level variability. Some embodiments may include a bandpass filter to remove low frequency shifts caused by changes in altitude (i.e. elevators) and high frequency shifts caused by cardiac induced thoracic changes. To ensure accurate triggering, an appropriate detection threshold must be set based on the physiologic parameter being measured, specific patient conditions, and any external influences on the signal being monitored. In the embodiment described here, evaluation of the patient's normal respiratory signals at the pressure sensor's implanted location allows appropriate setting of the trigger threshold.

The microprocessor 100 identifies the inspiration phase of the respiratory effort waveform from the digitized amplitude values from the pressure sensor so that the system can supply a shaped stimulus burst for the duration of that phase at the electrode 90. The onset of inspiration is characterized as a sustained increase in slope of the pressure waveform greater than a preset threshold but less than a maximum slope value. Generally, an inspiratory turn point would be indicated by an increase in the pressure signal amplitude of between about 1.5× and 5× a period of between 80 ms and 200 ms. The peak amplitude of the pressure signal indicates the end of inspiration and the onset of expiration. Generally, an inspiratory peak is detected if a negative slope for the pressure waveform is identified and sustained over about 60 to 150 ms. When varying the sample rate in accordance with the invention, the sample period for this application may be as long as ¼ of a second, and may decrease to 5 ms or less as the next anticipated inspiration approaches.

Alternatively, an analog derivative of the respiration pressure signal can be used to determine onset and offset of inspiration. In the analog mode of operation, the pressure sensor output can be processed by the IPG to derive a time derivative of the fluid pressure applied to the pressure sensor. A baseline value for the signal is then established by averaging about 10 consecutive voltage measurements. If the average is above the previous baseline by a predetermined voltage, then the baseline is reset to the average value. Once a valid baseline voltage has been established, a threshold voltage is established from the baseline voltage (e.g. baseline voltage minus a constant) that corresponds to the onset of inspiration. When the threshold voltage is achieved by the signal from the sensor, stimulation is enabled. In order to prevent false-positive indications of inspiratory onset, the signal voltage may be averaged and then compared with the threshold voltage. Inspiratory offset may be found in a similar manner by computing a second threshold voltage (i.e. a negative voltage characteristic of the expiratory phase of the respiratory cycle) and identifying the point at which the second threshold is achieved.

Accordingly, embodiments of the invention can include a method of operating an implantable medical device that includes sensing a physiological parameter of a patient. The physiological parameter is related to a periodically repeating physiological event. The sensed signal is sampled at a sampling frequency and a series of physiological events is detected. An expected time period between events is determined and the sampling frequency is increased ahead of expected events and decreased following detection of events.

Some embodiments of the invention include an implantable medical device with an implantable sensor for sensing a physiological parameter of a patient that provides an indication of respiration. The implantable medical device of these embodiments have an analog-to-digital converter for producing digital samples representative of the sensor signal at a sampling frequency and a processor for detecting the indication of respiration and an expected time period between the indications of respiration. The processor increases the sampling frequency ahead of an expected time of respiration.

In other embodiments in accordance with the invention, a method of operating an implantable medical device includes sensing a physiological parameter of a patient that includes a periodically repeating physiological event. The sensed signal is sampled at a selected sampling frequency to produce digital samples representative of the sensed signal. An expected signal period can be determined, the expected signal period being based on the amount of time between crossings of a threshold by the sensor signal and corresponding to the period between the periodically repeating physiological events. An expected time of each physiological event within each signal period is determined and the sampling frequency is increased ahead of an expected time of each physiological event and decreased following detection of each event.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

The invention claimed is:

1. A method of operating an implantable medical device, comprising:
   sensing a physiological parameter of a patient and producing a representative signal thereof, the physiological parameter including a periodically repeating physiological event;
   sampling the sensed signal at a selected sampling frequency to produce digital samples representative of the sensed signal;
   detecting the physiological events based on the digital samples;
   determining an expected time period between the physiological events; and
   setting the selected sampling frequency, the selected sampling frequency being increased ahead of an expected time of each physiological event based on the expected time period between physiological events, the selected sampling frequency being decreased following detection of each event.

2. A method according to claim 1, further comprising delivering a therapy to the patient at the expected time of each physiological event.

3. A method according to claim 1, further comprising delivering a therapy to the patient after detection of each physiological event.

4. A method according to claim 3, wherein the therapy includes electrical stimulation of upper airway muscles of the patient.

5. A method according to claim 1, wherein the physiological parameter includes an intrathoracic pressure in the patient.

6. A method according to claim 1, wherein the periodically repeating physiological event includes respiratory inspiration.

7. A method according to claim 1, wherein the determining the expected time period is based on the detection of the physiological events.

8. A method according to claim 1, further including detecting the frequency that the sensor signal crosses a measurement threshold value, the determining the expected time period between the physiological events being based on the frequency that the sensor signal crosses the measurement threshold value.

9. A method according to claim 1, wherein the increase of the selected sampling frequency includes increasing the sample frequency linearly with respect to time on the approach of the expected time of each physiological event.

10. A method according to claim 1, wherein the increase of the selected sampling frequency includes increasing the sample frequency exponentially with respect to time on the approach of the expected time of each physiological event.

11. A method according to claim 1, wherein the increase of the selected sampling frequency includes rapidly increasing the sampling frequency on the approach of the expected time of each physiological event.

12. A method according to claim 1, wherein the selected sampling frequency consists of first and second sampling frequencies, the second sampling frequency being higher than the first sampling frequency, then setting the sampling frequency being between the first and second sampling frequencies.

* * * * *